United States Patent
Takizawa et al.

(10) Patent No.: US 6,885,885 B1
(45) Date of Patent: Apr. 26, 2005

(54) MAGNETIC RESONANCE IMAGING METHOD AND DEVICE

(75) Inventors: Masahiro Takizawa, Chiba-ken (JP); Tetsuhiko Takahashi, Saitama-ken (JP)

(73) Assignee: Hitachi Medical Corporation, Tokyo (JP)

(*) Notice: Subject to any disclaimer, the term of this patent is extended or adjusted under 35 U.S.C. 154(b) by 0 days.

(21) Appl. No.: 09/979,241

(22) PCT Filed: May 26, 2000

(86) PCT No.: PCT/JP00/03384
§ 371 (c)(1),
(2), (4) Date: Feb. 20, 2002

(87) PCT Pub. No.: WO00/72752
PCT Pub. Date: Dec. 7, 2000

(30) Foreign Application Priority Data

May 26, 1999 (JP) .......................................... 11/147206

(51) Int. Cl.$^7$ ................................................ A61B 5/05
(52) U.S. Cl. ...................................................... 600/410
(58) Field of Search ................................ 600/410, 411, 600/407, 436, 419; 324/307, 308, 309

(56) References Cited

U.S. PATENT DOCUMENTS 6,118,273 A * 9/2000 Takizawa et al. ........... 324/309
6,242,914 B1 * 6/2001 Yoshitome .................. 324/309
6,541,970 B1 * 4/2003 Takizawa et al. ........... 324/309
6,704,594 B1 * 3/2004 Blank et al. ................ 600/423

* cited by examiner

Primary Examiner—Daniel Robinson
(74) Attorney, Agent, or Firm—Cooper & Dunham LLP (57) ABSTRACT

A magnetic resonance imaging apparatus has means for detecting the movement of an object so as to correct the variation of the non-uniformity of static magnetic field because of the movement of the object and thereby to improve the quality of the MR image. When actually measured data is corrected by using a signal for correcting the static magnetic field obtained in a preliminary measurement, the influence of the non-uniformity of static magnetic field is eliminated from the image based on the information from the body movement detecting means by using a correcting signal measured at the same time phase of the periodic movement as that of the actually measured signal. A navigation echo measured during the same repetition time as that of the actually measured signal is used for detection of time phase by detecting means. As a result, the quality of image is not deteriorated by the variation of the non-uniformity of static magnetic field due to the movement of the body of the object, realizing imaging of high quality image.

13 Claims, 8 Drawing Sheets

MAGNETIC RESONANCE IMAGING METHOD AND DEVICE

FIELD OF THE INVENTION

The present invention relates to magnetic resonance imaging (MRI) method and apparatus for measuring nuclear magnetic resonance signal (NMR signal) by making occurrence of nuclear magnetic resonance (NMR) phenomenon to atomic nucleus such as hydrogen or phosphorous in an object, and for imaging distribution of density or relaxation time of nuclear spin in said object, and especially to techniques that enable to perform effectively static magnetic field correction in case of imaging the object with motion.

BACKGROUND OF THE ART

MRI is an apparatus detecting NMR signals (echo signal) produced from the object by applying high frequency magnetic field to the object placed in the static magnetic field, and signal processing and imaging these signals. And high uniformity of the static magnetic field is demanded in order to get image of high quality. Especially in fast imaging method, such as single-shot type or multi-shot type of an echo planar imaging (EPI) method, echo signal to be necessary for reconstructing one image is acquired with only once or several times of nuclear spin excitation. Therefore high static magnetic field uniformity is demanded, because image quality acquired is influenced by uniformity of the static magnetic field.

In an MRI apparatus, static magnetic field is formed by static magnetic field generation means such as permanent magnet or super conducting magnet, and is maintained on high uniformity, but the uniformity varies according to the susceptibility of the object placed in the measurement space. It is proposed a method for removing the influence caused by the non-uniformity of the static magnetic field to the picture by signal processing. In this method, at a certain time before measurement for the formation of the image of the object, nuclear spin in imaging part of the object is excited by applying slice selective gradient magnetic field and high frequency magnetic field to the object. Then data for non-uniformity static magnetic field correction is previously acquired in the condition without application of phase encode gradient magnetic field. And echo signals (imaging data) are corrected by using this correction data.

Figure 5:
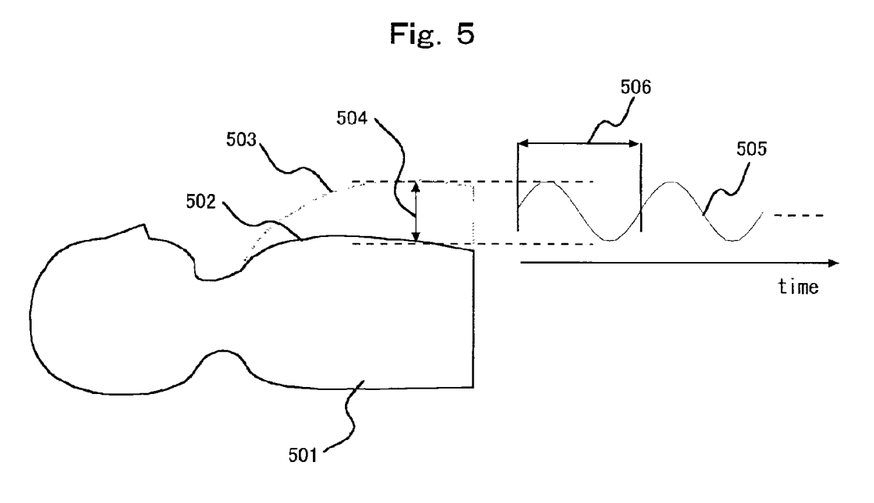
FIG. 5 is a view explaining the motion of the object.

On the other hand as shown in FIG. 5, if the object 501 moves during imaging such as breath motion 504, motion artifact accompanied with this is generated. This is a problem in the image. The reason why this motion artifact is generated is that the relationship between a location of organ and quantity of encode is varied between each echo signal by the movement of the object 501. This artifact appears to be a false image as if image is flowing through the whole screen, and it is a big obstacle in a clinical diagnosis.

As a method to remove this artifact, motion correction method using navigational echo is known. (for example, MAGNETIC RESONANCE IN MEDICINE, 35:895–902, June 1996, Seong-Gi Kim et. al, Fast Interleaved Echo-Planar Imaging with Navigator: High Resolution Anatomic and Functional Images at 4 Tesla).

By the way, in case of continuously imaging a region close to breast such as heart or lung field, if said motion correction method is performed together with said static magnetic field non-uniformity correction method, there is a case that static magnetic field non-uniformity correction method does not work effectively. That is, by the influence of the motion accompanied with breath motion of the object, static magnetic field non-uniformity is varied, too. However, data for static magnetic field non-uniformity correction previously measured does not include the change of static magnetic field non-uniformity by the motion of the object. So it is impossible to correct the measured echo signal accurately, even if static magnetic field non-uniformity correction is performed.

Thus the object of the present invention is to improve the correction accuracy in case of removing the influence of static magnetic field non-uniformity from image using correction data.

In addition, other object of the present invention is to provide an MRI apparatus, which can acquire high quality image by combining effectively the motion correction method and static magnetic field correction method.

DISCLOSURE OF THE INVENTION

A method invention to achieve said object in the present invention is disclosed as follows. The first magnetic resonance imaging method comprises, the first step for applying static magnetic field, slice selective gradient magnetic field, gradient magnetic field for reading out a signal to an object placed in a measuring space with the defined pulse sequence, and acquiring signal showing non-uniformity distribution of the static magnetic field in selected slice of said object, the second step for applying static magnetic field, slice selective gradient magnetic field, phase encode gradient magnetic field, gradient magnetic field for reading out the signal to said object placed in the measuring space with the defined pulse sequence and acquiring signal showing image information in the selected slice of said object, the third step for making signal showing real image information of said object by calculating between signal showing image information acquired in said second step and signal showing static magnetic field non-uniformity acquired in said first step, and the fourth step for reconstructing image of said object from signal showing real image information of said object.

And the second method invention to achieve said object in the present invention is disclosed as follows. This second magnetic resonance imaging method comprises, the fifth step for applying static magnetic field, slice selective gradient magnetic field, gradient magnetic field for reading out the signal to the object placed in the measuring space with the defined pulse sequence and for acquiring signal showing static magnetic field non-uniformity in selected slice of the object, the sixth step for detecting a motion of the object and setting plural number of time phase in one period of a motion of the object, and acquiring MR signal showing the motion of the object in these every time phase, the seventh step for applying static magnetic field, slice selective gradient magnetic field, phase encode gradient magnetic field, gradient magnetic field for reading out the signal with the defined pulse sequence to the object placed in the measurement space in each time phase of the one period of the motion of the object, and for acquiring signal that shows image information in the selected slice of the object, and the eighth step for removing static magnetic field non-uniformity signal including static magnetic field non-uniformity from the signal showing image information of the object being acquired in said seventh step in each time phase by using the signal showing static magnetic field acquired in said the fifth step and the signal showing the motion of object acquired in said the sixth step, and the ninth step for reconstructing image by using the signal being removed static magnetic field non-uniformity in said the eighth step.

And a magnetic resonance imaging method as the third method invention to achieve said object in the present invention is disclosed as follows. The third magnetic resonance imaging method comprises, the tenth step for detecting motion of the object and for setting several time phase in one period of the motion of this object, the eleventh step applying static magnetic field, slice selective gradient magnetic field, gradient magnetic field for reading out the signal to the object placed in the measuring space with the defined pulse sequence per each time phase, and for acquiring signal expressing motion of the object and signal of static field non-uniformity distribution of the selected slice, the twelfth step applying static magnetic field and slice selective gradient magnetic field and gradient magnetic field for reading out the signal with the defined pulse sequence to the object placed in the measuring space per each time phase, and acquiring signal showing the motion of the object and image information in the selected slice, the thirteenth step removing static magnetic field non-uniformity signal comprising static magnetic field non-uniformity by the motion of the object from signal showing image information of the object per each time phase acquired in said eleventh step using signal expressing motion of the object acquired in the eleventh step and signal showing non-uniformity distribution of the static magnetic field in the selected slice and signal expressing motion of the object acquired by said eleventh step, and the fourteenth step for performing image reconstruction by using signal of which static magnetic field non-uniformity is removed in said thirteenth step.

And moreover a magnetic resonance imaging method as the forth method invention to achieve said object in the present invention is disclosed as follows. The fourth magnetic resonance imaging method comprises, the fifteenth step for detecting the motion of the object, and for setting plural number of time phase in one period interval of a motion of the object, the sixteenth step applying static magnetic field and slice selective gradient magnetic field and gradient magnetic field for reading out the signal to the object placed in the measurement space with the defined pulse sequence, and for acquiring signal expressing motion of the object and signal showing non-uniformity distribution of the static magnetic field in the selected slice, the seventeenth step for applying static magnetic field and slice selective gradient magnetic field and gradient magnetic field for reading out the signal to the object placed in the measurement space with the defined pulse sequence in every time phase being set, and for acquiring signal expressing the motion of the object and signal showing image information in the selected slice, the eighteenth step for detecting signal showing irregular motion of the object from the signal expressing motion of the object acquired by said sixteenth or seventeenth step and for removing this detected irregular motion signal from image information acquired in said seventeenth step, the nineteenth step removing static field non-uniformity signal from signal having be removed irregular motion signal in said eighteenth step by using signal expressing motion of the object acquired by said sixteenth step and seventeenth step and signal showing static magnetic field non-uniformity distribution in the selected slice and signal expressing the motion of the object per every time phasing being set, and twentieth step for image reconstructing signal acquired in said nineteenth step.

In addition, as an apparatus invention to achieve said object, and to realize said first method invention to said forth method invention is disclosed. That is, an magnetic resonance imaging apparatus disclosed as the first apparatus invention comprises, magnetic field generation means for generating static magnetic field and gradient magnetic field and high frequency magnetic field to the space that the object is placed, detecting means for detecting nuclear magnetic resonance signal generated from one object, signal processing means for signal processing nuclear magnetic resonance signal detected by said detecting means, means for image reconstructing signal processed by this signal processing means, image display means for displaying the reconstructed image, means for applying static magnetic field and slice selective gradient magnetic field and gradient magnetic field for reading out the signal to the object placed in the measurement space with the defined pulse sequence and for acquiring signal showing non-uniformity of the static magnetic field in the selected slice of the object, means for applying static magnetic field and slice selective gradient magnetic field and phase encode gradient magnetic field and gradient magnetic field for reading out the signal to the object placed in the measurement space with the defined pulse sequence and for acquiring signal showing image information in the selected slice of the object, means for removing signal showing the static magnetic field non-uniformity from signal showing the image information and for making signal expressing real image information of the object, and means for reconstructing image of the object from the signal expressing real image information of the object.

And a magnetic resonance imaging apparatus as the second apparatus invention to achieve said object comprises, magnetic field generation means for generating static magnetic field and gradient magnetic field and high frequency magnetic field to the space in which the object is placed, detecting means for detecting nuclear magnetic resonance signal being generated from the object, signal processing means for signal processing nuclear magnetic resonance signal detected by said detecting means, image reconstruction means for image reconstructing the signal processed by this signal processing means, image display means for displaying image reconstructed by said image reconstructing means, means for applying static magnetic field and slice selective gradient magnetic field and gradient magnetic field for reading out the signal to the object placed in the measurement space with the defined pulse sequence and for acquiring signal showing non-uniformity distribution of the static magnetic field in the selected slice of the object, means for detecting motion of the object by setting plural number of time phase in one period interval of the motion of the object and acquiring an MR signal showing motion of the object per these each time phase, means for applying static magnetic field and slice selective gradient magnetic field and phase encode gradient magnetic field and gradient magnetic field for reading out to the object placed in the measurement space in each time phase in one period interval of the motion of the object with the defined pulse sequence and for acquiring signal showing image information in the selected slice of the object, means for removing static magnetic field non-uniformity signal including static magnetic field non-uniformity of the motion of the object from signal showing image information of the object in each time phasing by using said signal showing static magnetic field non-uniformity and signal showing motion of the object, means for performing image reconstruction using signal that the static field non-uniformity signal is removed.

And a magnetic resonance imaging apparatus as the third apparatus invention to achieve said object comprises, the magnetic field generation means for respectively generating static magnetic field and gradient magnetic field and high frequency magnetic field to the space in which object is placed, detecting means for detecting nuclear magnetic resonance signal generated from the object, signal processing means for signal processing the nuclear magnetic resonance signal detected by said detecting means, means for image reconstructing the signal processed by said signal processing means, image display means for displaying reconstructed image, means for detecting the motion of the object and setting plural number of time phase in one period interval of the motion of this object, means for applying static magnetic field and slice selective gradient magnetic field and gradient magnetic field for reading out the signal to the object placed in the measurement space with the defined pulse sequence in each time phase that is set and for acquiring signal expressing motion of the object and signal showing non-uniformity distribution of the static magnetic field in the selected slice, means for applying static magnetic field and slice selective gradient magnetic field and gradient magnetic field for reading out the signal to the object placed in the measurement space with the defined pulse sequence per time phase that is set and for acquiring the signal expressing the motion of the object and the signal showing the image information in the selected slice, means for removing static magnetic field non-uniformity signal including static magnetic field non-uniformity by the motion of the object from the signal showing image information of the object in each time phase by using signal expressing motion of the object and signal showing non-uniformity distribution of the static magnetic field in the selected slice and signal expressing motion of the object that is acquired together with the imaging signal, and means for performing image reconstructing by using signal that the static field non-uniformity signal is removed.

Moreover a magnetic resonance imaging apparatus as the fourth apparatus invention to achieve said object in the present invention is disclosed as follows, magnetic field generation means for generating static magnetic field and gradient magnetic field and high frequency magnetic field respectively to the space in which the object is placed, detecting means for detecting nuclear magnetic resonance signal generated from the object, signal processing means for signal processing the nuclear magnetic resonance signal detected by said detecting means, means for image reconstructing said signal processed by this signal processing means, image display means for displaying reconstructed image, means for detecting motion of the object and setting plural number of time phase in one period interval of the motion of the object, means for applying static magnetic field and slice selective gradient magnetic field and gradient magnetic field for reading out the signal with the defined pulse sequence in each time phase that is set and acquiring signal expressing motion of the object and non-uniformity distribution of the static magnetic field in the selected slice, means for applying static magnetic field and slice selective gradient magnetic field and gradient magnetic field for reading out the signal with the defined pulse sequence in each time phase set and acquiring signal expressing motion of the object and signal showing image information in the selected slice, and means for detecting signal showing an irregular motion of the object from signal expressing the motion of the object and removing this detected irregular motion signal from image information, means for removing static magnetic field non-uniformity signal from image signal that the irregular motion signal is removed by using signal expressing motion of the object and signal showing non-uniformity distribution of the static magnetic field in the selected slice and signal expressing motion of the object in each time phase that is set, and means for image reconstructing from signal that the static magnetic field non-uniformity signal is removed.

BEST MODE OF CARRYING OUT THE INVENTION

Hereinafter, one embodiment of the present invention will be explained referring to drawings.

Figure 4:
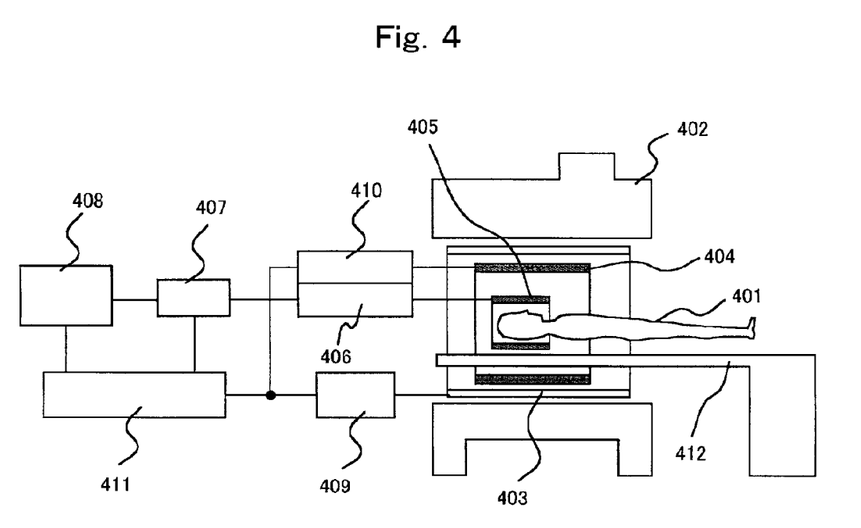
FIG. 4 is a view that illustrates entire composition of the MRI apparatus applied the present invention.

FIG. 4 shows composition of the typical MRI apparatus applied in the invention. This MRI apparatus comprises magnet 402 that generates static magnetic field to the measuring space in which the object 401 is placed, gradient magnetic field coil 403 that generates gradient magnetic field to this space, RF coil 404 that generates high frequency magnetic field to this space, RF probe 405 that detects NMR signal which is generated from object 401, and bed 412 that conveys the object 401 in the measuring space.

Gradient magnetic field coil 403 is comprised of X, Y, Z gradient magnetic field coil to three directions. And each gradient magnetic field coil generates gradient magnetic field respectively in accordance with the signal supplied from gradient magnetic field electric power supply 409. Each generated gradient magnetic field is superimposed to static magnetic field that is generated by magnet 402. RF coil 404 generates high frequency magnetic field corresponding to signal supplied from RF transmission part 410 and excite nuclear spin in the object 401. The NMR signal that is generated from excited nuclear spin is detected by RF probe 405 and in signal detection part 406, and detected signal is processed in signal procession part 407, thereafter it is converted to image signal by calculation. The image signal is displayed as an image to display part 408.

Operation of the gradient magnetic field power supply 409 and RF transmission part 410 and the signal detection part 406 are controlled by control part 411 in accordance with a timing chart, which is generally called pulse sequence. For this purpose software is stored in control part 411.

Figure 1:
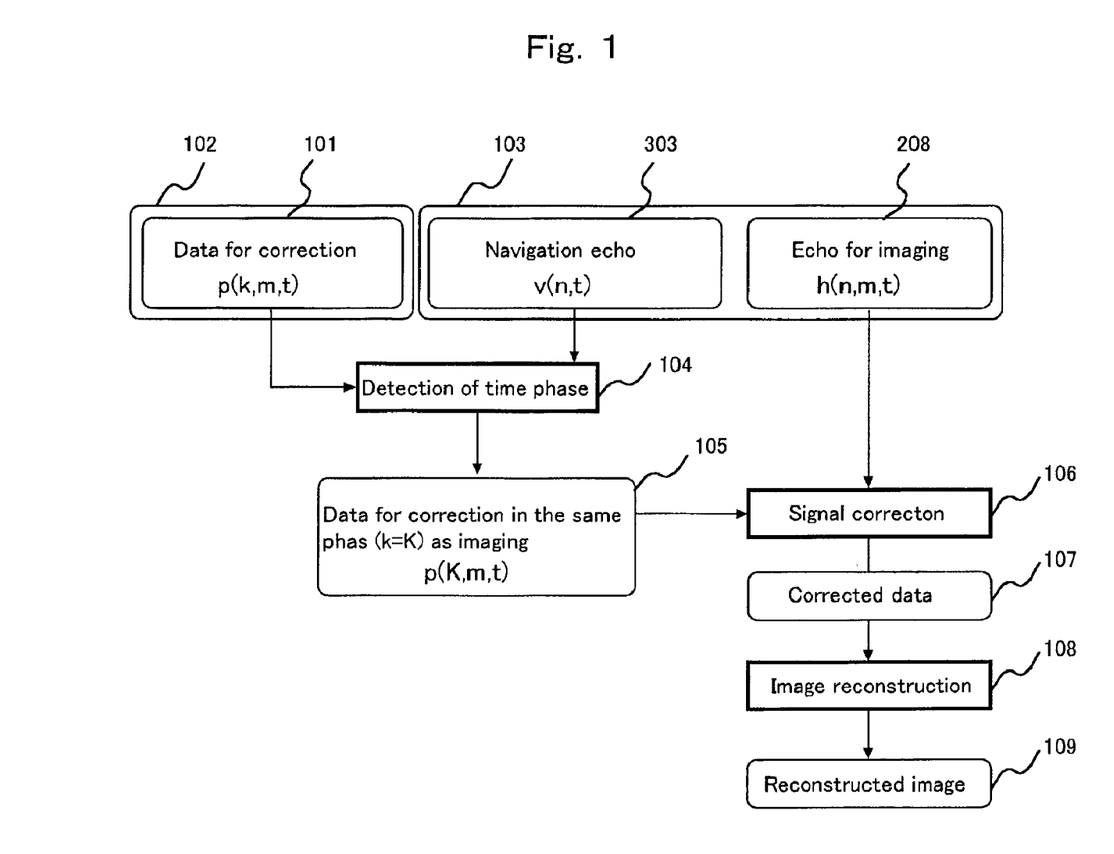
FIG. 1 is a view that illustrates one embodiment of signal processing performed in the MRI apparatus of the present invention.

Next, a method for imaging continuously the plural number of images in the MRI apparatus of these compositions will now be explained. FIG. 1 is a view illustrating first embodiment of the invention. This imaging method comprises step 102 for acquiring signal for correcting static magnetic field non-uniformity, step 103 for acquiring echo for imaging, and step 104, 106, 108 for signal processing and image reconstruction using these signals. At first after performing preliminary measurement before imaging of the object, correction signal for removing influence of static magnetic field non-uniformity from measured signal for imaging.

Figure 2:
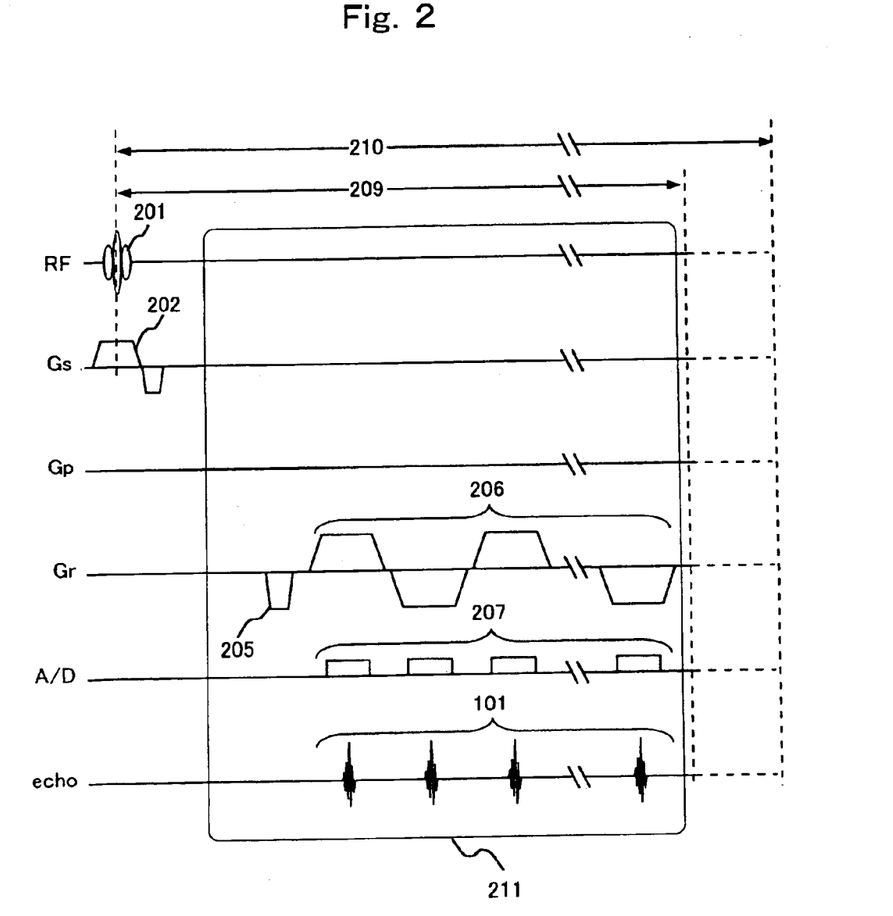
FIG. 2 is a view that illustrates one example of pulse sequence of preliminary measurement performed in the MRI apparatus of the invention.
Figure 6:
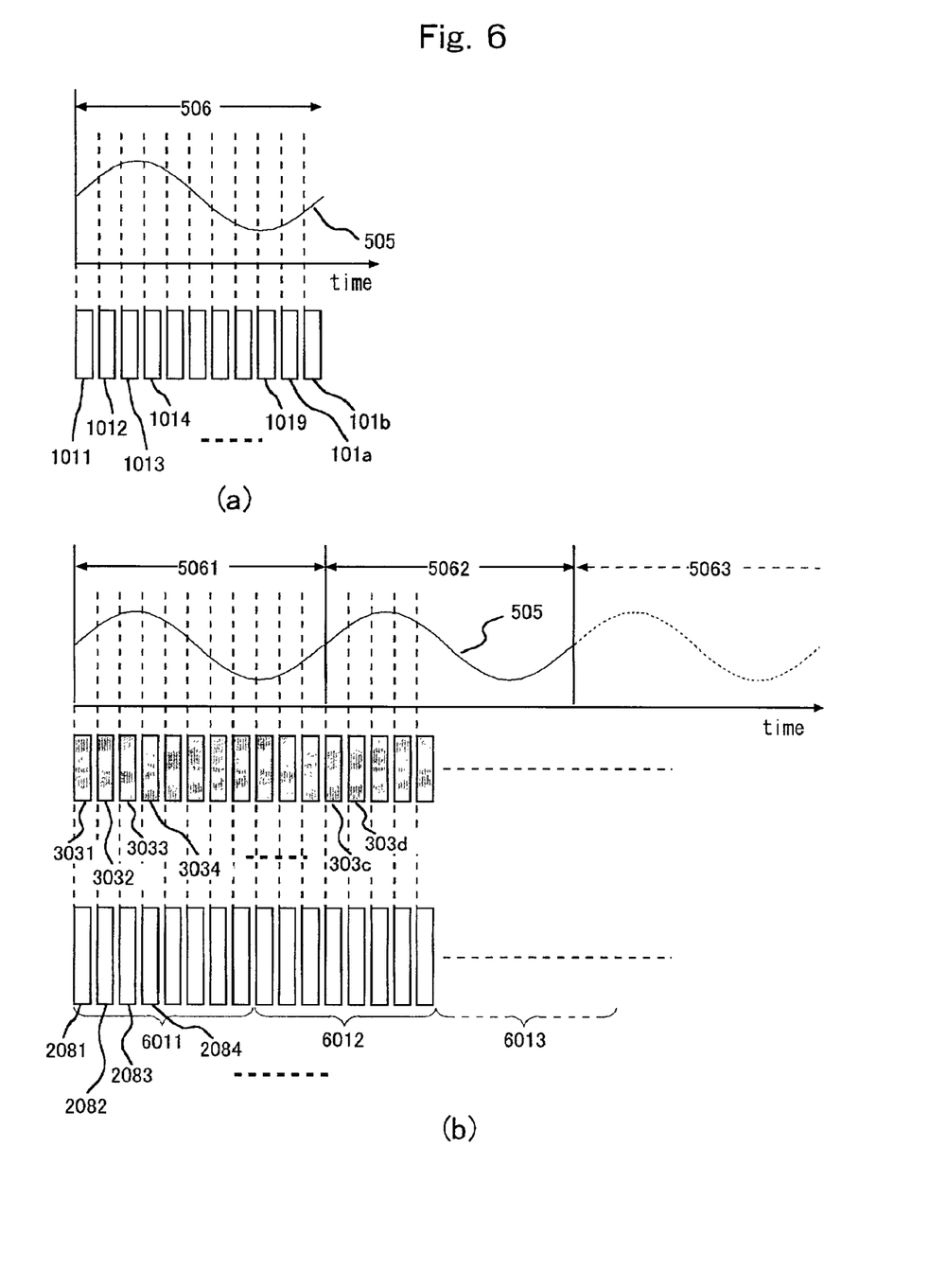
FIG. 6 is a view conceptually explaining the signal acquired in an embodiment shown in FIG. 1.

FIG. 2 is view illustrating one example of pulse sequence for acquiring signal 101 for correcting static magnetic field non-uniformity by step 102 in FIG. 1. This pulse sequence is based on multi-shot type EPI sequence. But pulse sequence shown in FIG. 2 is different from EPI sequence that is performed later, in the point that it measures plural number of echo signal without applying phase encode gradient magnetic field. That is, at first irradiating high frequency pulse 201 (RF pulse) to the object 401 including magnetization that is detected, at the same time, applying gradient magnetic field (Gs pulse) 202 for selecting slice, nuclear spin in the slice for imaging is selectively excited. Next applying gradient magnetic field pulse (Gr pulse) 206 of which polarity is alternated continuously, echo signal 101 generates in time series in each period of the alternated Gr pulse 206. So sampling this in time range 207 respectively, a series of data in time 101 is acquired. By repeating those sequence 209 several times, correction data p (k, m, t) 101 corresponding to one image data (Herein, k expresses repeating number (shot number), m expresses which number the signal is measured (measuring number), t expresses time.) is acquired. This sequence 209 is performed at least number of times that one period of the motion of the object (506 in FIG. 5) divide with repetition time of sequence 209, although this sequence 209 varies with the length of sequence 209. In the embodiment, this sequence 209 is repeated 11 times as shown in FIG. 6(*a*).

Figure 3:
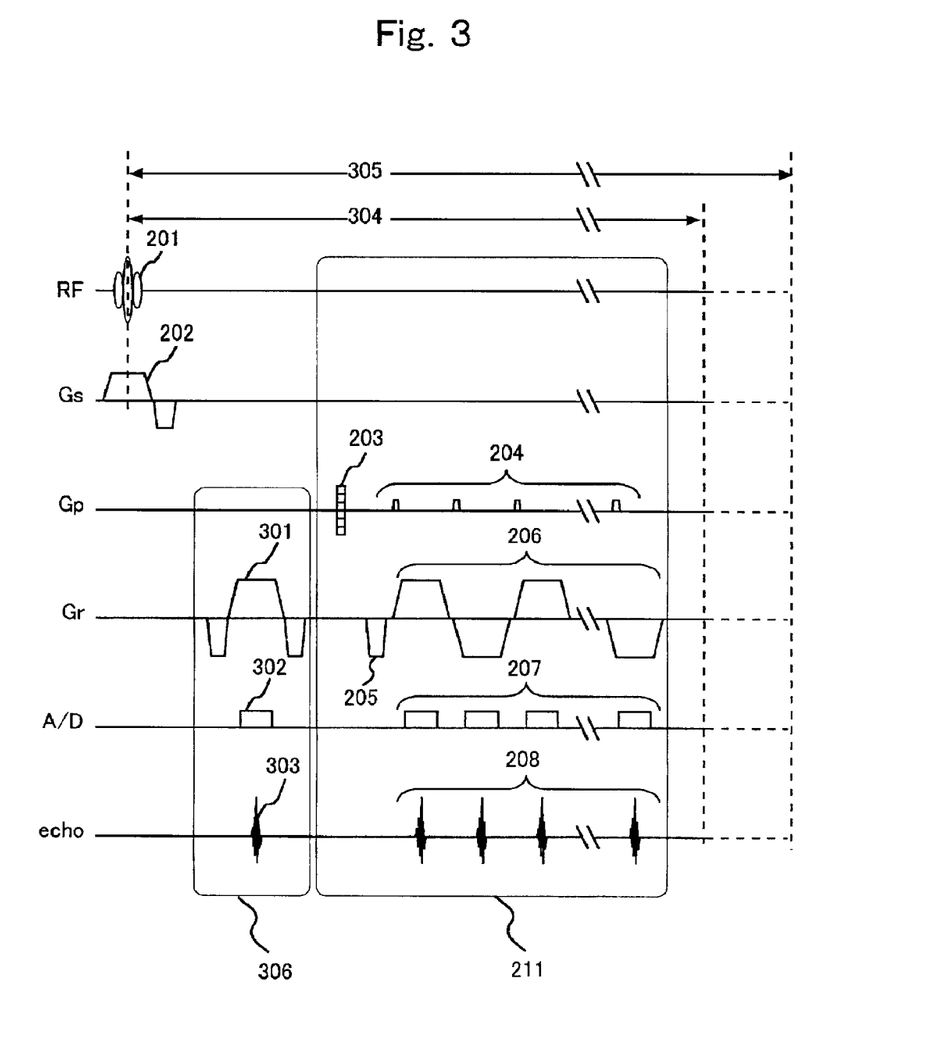
FIG. 3 is a view that illustrates one example of a pulse sequence for measurement to imaging performed in the MRI apparatus of the present invention.

In this way, measurement for imaging is performed after acquiring static magnetic field non-uniformity correction data (step 103 in FIG. 1). FIG. 3 shows one example of pulse sequence to be used for imaging. This pulse sequence is also the multi-shot type EPI sequence, but, in this pulse sequence, moreover the step 306 for measuring navigation echo 303 is added in the interval from excitation of the nuclear spin to generation of the first echo signal for the imaging.

That is, in this pulse sequence, after having applied RF pulse 201 and Gs pulse 202, Gr pulse 301 is applied before measurement for imaging 211, navigation echo 303 is measured in time range 302. This navigation echo 303 is a signal without phase encoded, but the shape orbital is preferable. In addition, if the time for measuring imaging echo signal decreases in the range of repetition time for measuring navigation echo, and problem such as being unable to get enough imaging echo number occurs, it is preferable to keep number of echo signal for the imaging by intensifying a little the strength of the gradient field for reading out the echo signal for the imaging. In this case it is necessary to change pulse sequence for measuring the correction signal by accordance with the pulse sequence for imaging.

Next, Gp pulse 203 is applied to give offset for the phase encoding, and Gr pulse 205 is applied to give an offset of gradient magnetic field for reading out signal. Echo signal 208 having given each phase encode value is sampled in each period of the polarity inversion Gr pulse 206 during the Gp pulse 204 is applied discretely, then the data for imaging is measured. Each echo signal composing this measured data, are correspondence with generation time of each echo signal of the static magnetic field non-uniformity correction data and shown in FIG. 2. That is, in comparison with FIG. 2 and FIG. 3, each echo signal of correction data 101 and imaging data 208 are occurred at the same time after excitation.

By repeating these pulse sequence 304 several times, navigational echo v (n, t) 303 and imaging echo h (n, m, t) 208 are acquired every each repetition. But herein, n is repetition number (shot numbering), t is time, and m is the measuring number. For example, if the number of the echo signal for imaging 208 measured after applied one time of high frequency pulse is 16, the number of data to reading out direction per 1 echo signal is 128, the number of encode to phase encode direction is 128, then the repetition number (number of shot) being necessary for acquiring one image is 8. And imaging is performed continuously with a unit of 8 shots.

Next signal processing and image reconstruction are performed by, using signal measured in the preliminary measurement and the measurement for imaging (106,108 in FIG. 1). In order to remove influence of static magnetic field non-uniformity from imaging echo signal, in correction data 101 and imaging echo 208, it is possible by correcting calculation between data of the same time phase, for example by subtracting correction data from imaging echo of the same time phase. For this purpose, one dimensional Fourier transforming the correction data 101 and imaging echo 208 respectively to the reading out direction, and looking for the absolute profile of which the width and location are the same, and performing correspondence between correction data and imaging echo in the same time phase, it is preferable to perform correcting calculations between these pairs of signals.

In FIG. 6, (a) is a view illustrating conceptually static magnetic field non-uniformity correction data 101, which was acquired before measurement for imaging. In this example, 11 of correction data 1011, 1012, . . . 1019, 110a, 101b are acquired in one period interval of the breathing of the object 506. Accordingly, each correction data is measured respectively in different time phase of one period interval 506 of the motion 505. And, FIG. 6 (b) is a view illustrating conceptually the navigation echo and the imaging echo those were acquired in the measurement for imaging. And a set by dotted line (3031 and 2081, 3032 and 2082, \* \* \* ) is a set acquired in the same repetition, that is, it is a set of navigation echo and imaging echo of which shot number n are equal. In this case, in order to acquire one image, 8 sets of signals are measured. And for acquiring images continuously in time, set of signals 6011,6012,6013, \* \* \* are acquired repeatedly.

These set of signals are also measured in different time phase in each period 505 of the motion. But, the acquiring time of each set of signal is not always consistent with one period of the movement of the object 5061, 5062, 5063, \* \* \* , so detection(monitoring) of the time phase is performed out as follows.

Thus at first, time phasing is detected by comparing correction data 101 and navigational echo 303 (step 104 of FIG. 1). Because phase encode gradient magnetic field is not applied to both the navigational echo 303 and correction data 101, after one-dimensional Fourier transformation (FFT) to the reading out direction was performed respectively, data of the same time phase specified by comparing width and location of those absolute profile. In addition, because in this embodiment the time from excitation of the nuclear spin to generation of signal is not strictly the same between each echo signal of correction data 101 and navigational echo 303, so specification of the time phase is performed by selecting signal that close most. And in this method, it is necessary that the correction data 101 and navigational echo 303 are measured by applying gradient magnetic field for reading out of the same axis. The reason is that comparison of the width and location is possible by one-dimensional FFT in the same axis in which signal is measured.

In this place, correction data detected in the same time phase as the navigational echo v (n, t) at certain time phase (time phase k=K) is outputted as correction data p (K, m, t) 105 which is imaging echo h (n, m, t) acquired in the same time phase and in the same repetition period in which the navigation echo is acquired (In other word n is the same). But in an example shown in FIG. 6, at cycle 5061 of a motion, the time phasing is detected by correspondence correction data from 1011 to 101b with navigation echo from 3031 to 303b. And at cycle 5062, time phase is detected by correspondence correction data from 1011 to 101b with navigation echo acquired at cycle 5062 that follows 303c. But, in case of referring this correction in image unit, at the correction of the image signal 6011, time phase detection and correction of the image signal are performed by from 1011 to 101b of the correction data and from 3011 to 3038 of the navigation echo. And at next image signal 6012, time phase detection and correction of the image signal are performed by from 1011 to 101b of correction data 1011 and eight navigation echoes those follow 3039.

Next using this correction data p (K, m, t) 105, static magnetic field non-uniformity element of the imaging echo h (n, m, t), which is the same time phase as the correction use data is corrected (step 106 in FIG. 1).

For example, as a procession of signal correction, one dimensional Fourier transforming correction data p (K, m, t) and imaging echo h (n, m, t) to p (K, m, x), H (n, m, x) (x expresses position of the reading out direction.) and performing calculation as the following equation, corrected data H (n, m, x) is acquired.

$$re[H'(n,m,x)]=(re[H(n,m,x)]re[P(K,m,x)]+im[H(n,m,x)]im[P(K,m,x)])/|P(K,m,x)|$$

$$im[H'(n,m,x)]=(im[H(n,m,x)]re[P(K,m,x)]-re[H(n,m,x)]im[P(K,m,x)])/|P(K,m,x)|$$

(In these equations, re [ ] expresses real part of the signal, im [ ] expresses imaginary part of the signal, | | expresses absolute value of the signal, respectively.)

Said steps from the detection of time phase to the signal detection are performed to the every imaging echo that is measured continuously, and corrected data 107 is acquired.

Next, image reconstruction is performed by, using corrected data 107 (step 108), and reconstructed image 109 is outputted. By doing this, static magnetic field non-uniformity corrected image is displayed continuously.

Next by using FIG. 7 and FIG. 8, the second embodiment of the invention will now be explained. In this embodiment, preliminary measurement for measuring static magnetic field non-uniformity correction signal is performed before imaging. This is the same as said embodiment. In the preliminary measurement of this embodiment, the step for measuring navigation echo is added, although view of pulse sequence is omitted. That is, this embodiment is to perform preliminary measurement of pulse sequence to measure correction signal without applying phase encode gradient magnetic field after measuring navigation echo 303 in pulse sequence FIG. 3 shown in said first embodiment. And after that the pulse sequence in FIG. 3 is performed for imaging.

That is, in the pulse sequence in FIG. 2 of this embodiment, after applying RF pulse 201 and Gs pulse 202, nuclear spin in the slice is excited selectively in the object 401. Navigational echo 701 is measured by applying Gr pulse without applying Gp pulse (this is not illustrated in FIG. 2). Next plural number of correction data 101 is acquired, by applying polarity reversing pulse 206. By repeating this operation k times, data set of correction data p (k, m, t) 101 and navigational echo pv (k, t) is acquired (step 702). In FIG. 8(a), these correction data 1011,1012, * * * and navigational echo 7011,7012, * * * are shown.

Next, imaging is performed. This imaging is the same as step 102 in the embodiment shown in FIG. 1. And performing pulse sequence shown in FIG. 3, data set of navigation echo 303 and imaging echo 208 are acquired (step 703). Next by comparing a navigation echo 303 in a data set of imaging with navigation echo 701 in a data set for correction, time phase is detected (step 704). In the time phase detection method in this second embodiment, timing from excitation of the nuclear spin until appearance of echo in compared navigation echo are all consistent, so time phase is detected more precisely than the first embodiment. It is preferable to detect the time phase in this case by one-dimensional fast Fourier transforming each navigation echo as same as the embodiment in FIG. 1 and then comparing width and location of the absolute profile. But it is possible to detect by compare navigation echo their selves without signal processing. In this case, amount of calculation for correction processing is small enough.

The correction data corresponding to detected time phase (we define k=K) is outputted as a data p (K, m, t) 105 for correcting imaging echo of the same time phase. Such detection of time phase (output of the correction data of the same time phase) is performed to the entire imaging echo. And after that signal correction (step 106), image reconstruction (step 108) are performed as same as the embodiment in FIG. 1, and reconstructed image is acquired (step 109).

In this embodiment, navigational echo 701 is also acquired in the preliminary measurement. And time phase is detected by comparing navigation echo of preliminary measurement with that of imaging. Therefore, it is possible to make amount of signal processing (amount of calculation) small. In addition, because it is possible to select the axis for acquiring navigation echo (reading out direction of the gradient magnetic field) in the preliminary measurement and imaging to the arbitrary direction without relating to the imaging echo and correction data, it is possible to set acquiring axis for navigation echo to the direction in case of which the object motion is problem.

Figure 9:
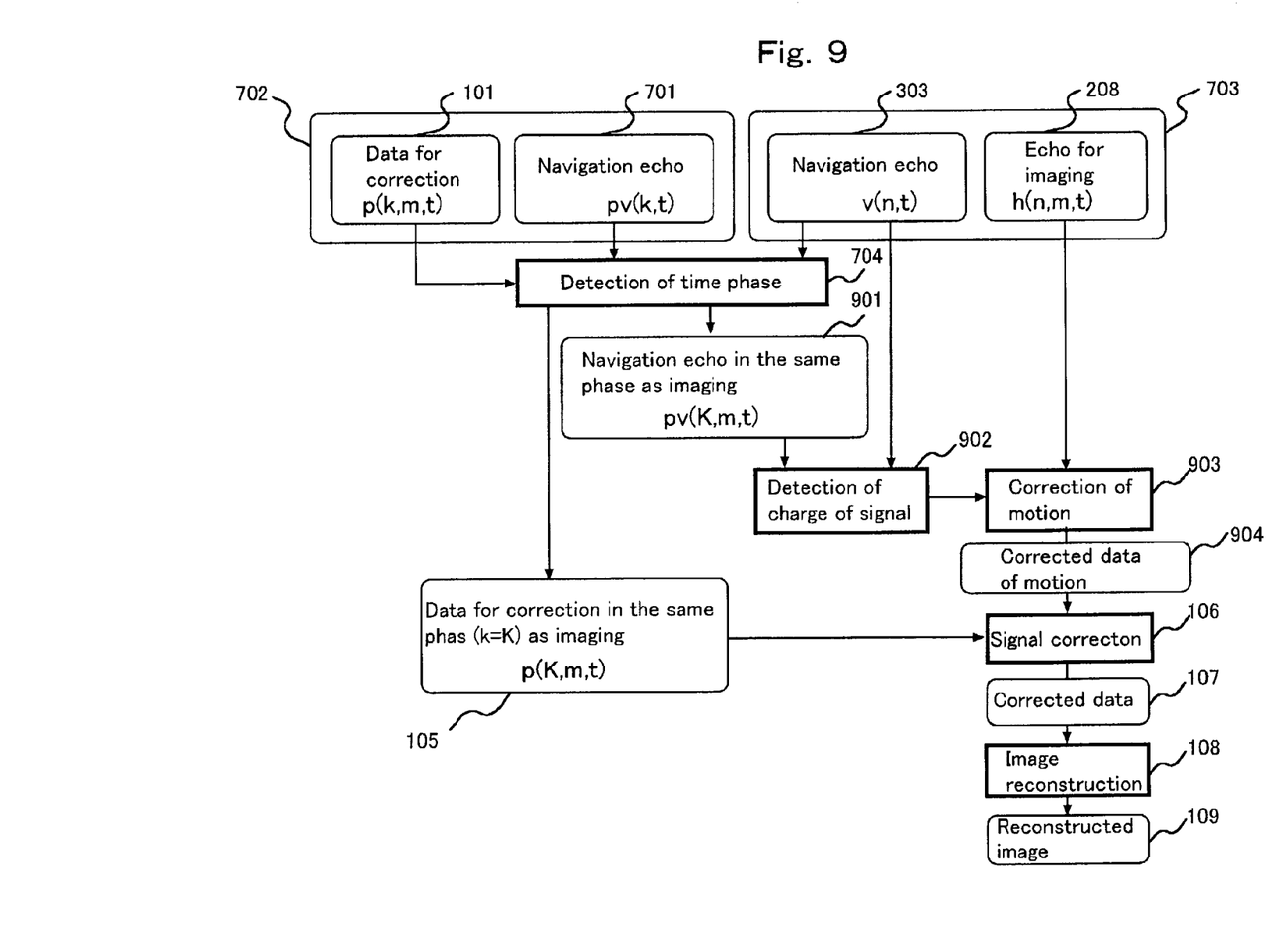
FIG. 9 is a view illustrating other example of the signal processing performed in the MRI apparatus of the invention.

Furthermore, the third embodiment of the present invention will be explained using FIG. 9. This embodiment is also the same as the embodiment shown in FIG. 7 in the point that has step 702, 703 acquiring data set including navigation echo in both preliminary measurement and imaging. But the difference with an embodiment in FIG. 7 is that it has a motion correction step 903 before signal correction step 106.

In this embodiment, in the step 704 to detect time phase by comparing navigation echo 701 in the preliminary measurement with navigation echo 303 in imaging, correction data p (K, m, t) 105 which is the same time phase as the imaging echo h (K, m, t) that should be corrected is outputted, together navigation echo pv (K, m, t) that is the same time phase as the imaging data 208 is outputted. From this navigation echo 901 and navigation echo 303 that is measured in the same repetition as the imaging echo, signal change by the motion of the object is obtained (step 902). And by using this change, emotion correction to the imaging echo is performed (step 903). Then emotion corrected data 904 is acquired.

For signal change detection process 902 for correcting emotion, well known technique to correct emotion using navigation echo can be adopted. For example, we can adopt such method as follows. One is the correction method in which the phase difference is obtained between navigation echo 701 and 303 in the measurement space and corrects the imaging echo based on the phase difference in the measurement space. And second is the correcting method such as obtaining phase difference by one-dimensional fast Fourier transforming the navigation echoes 701 and 303 in the hybrid space and correcting imaging echo based on the phase difference.

Figure 7:
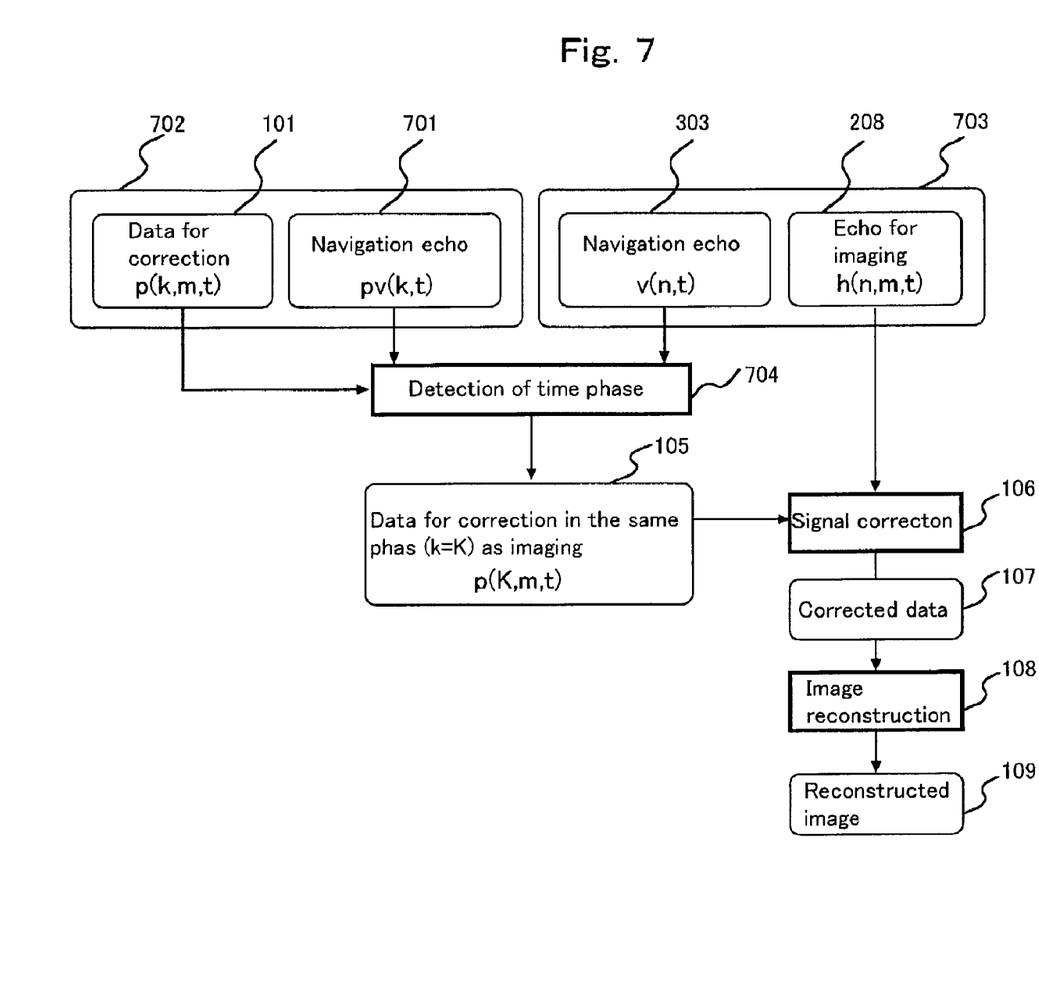
FIG. 7 is a view illustrating another embodiment of signal processing performed in the MRI apparatus of the present invention.
Figure 8:
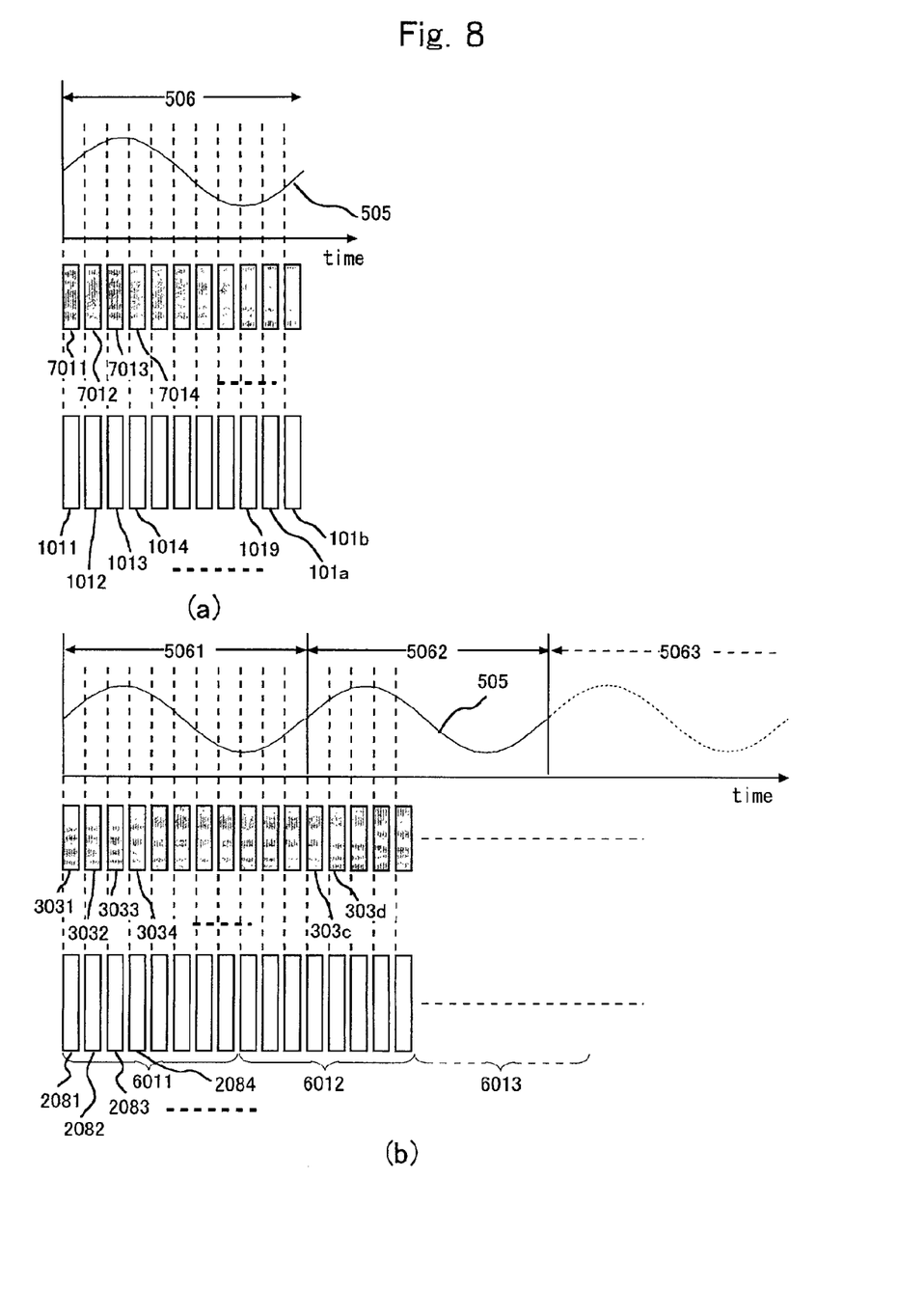
FIG. 8 is a view conceptually explaining the signal acquired in an embodiment shown in FIG. 7.

As thus described, after having corrected the emotion of the object in the imaging echo, performing the signal correction of static field non-uniformity by using correction data 105 that is the same time phasing as the imaging echo and reconstructing image are the same as the embodiment in FIG. 1 and FIG. 7. In this embodiment, because emotion correction is performed by using navigation echo that is acquired in the preliminary measurement, it is possible to perform static field non-uniformity correction precisely even in case of periodic motion with other emotion from correction data acquisition to imaging echo acquisition.

The present invention is not limited the previous described embodiment. Accordingly, any and all modification, variation or equivalent arrangements to those skilled in the art should be considered to be within the scope of the invention. For example, although multi shot type EPI sequence is explained in said embodiment, but it is possible to apply this invention to one shot type EPI sequence or burst sequence or spectroscopic sequence and so on. In addition, as a means for detecting time phase of the emotion, although an example using navigation echo is explained, but it is possible to use sensor. In this case, it is possible to select correction signal of the same time phase by using synchronizing technique such as breath synchronization.

According to the invention described above, because it is possible to correct static magnetic field non-uniformity of the measurement signal by using correction signal measured in the same time phase as the motion of the object based on the information from the means for detecting the motion of the object, it is possible to prevent deterioration MR image caused by the change of static magnetic field non-uniformity with motion of the object such as breath motion. Doctor is able to diagnose the object based on high quality MR images.

What is claimed is:

1. Magnetic resonance imaging method comprising,
   (a) step for applying static magnetic field, slice selective gradient magnetic field, gradient magnetic field for reading out a signal to an object placed within a measurement space with a defined pulse sequence, and for acquiring signal showing non-uniformity distribution of said static magnetic field in selected slice of said object,
   (b) step for applying said static magnetic field, slice selective gradient magnetic field, phase encode gradient magnetic field, gradient magnetic field for reading out said signal to said object placed in said measurement space with said defined pulse sequence, and for acquiring signal showing image information in said selected slice of said object,
   (c) step for making signal showing real image information of said object by calculating between signal showing image information acquired in said step (b) and signal showing static magnetic field non-uniformity acquired in said step (a),
   (d) step for reconstructing image of said object from signal showing real image information of said object.

2. Magnetic resonance imaging method comprising,
   (e) step for applying static magnetic field, slice selective gradient magnetic field, gradient magnetic field for reading out said signal to an object placed in measurement space with defined pulse, and for acquiring signal showing static magnetic field non-uniformity in said selected slice of said object,
   (f) step for detecting motion of said object and for setting plural number of time phase in one period of a motion of said object, and for acquiring MR signal that shows said motion of said object in these every time phase,
   (g) step for applying static magnetic field, slice selective gradient magnetic field, phase encode gradient magnetic field, gradient magnetic field for reading out said signal with the defined pulse sequence to said object placed in said measurement space in each time phase of said one period of said motion of said object, and for acquiring signal that shows image information in said selected slice of said object,
   (h) step for removing static magnetic field non-uniformity signal including static magnetic field non-uniformity from said signal showing image information of said object being acquired in said step (g) in each time phase by using said signal showing static magnetic field acquired in said step (e) and said signal showing said motion of object acquired in said step (f),
   (i) step for reconstructing image by using said signal being removed static magnetic field non-uniformity in said step (h).

3. Magnetic resonance imaging method comprising,
   (j) step for detecting motion of an object and for setting several time phase in one period of said motion of said object,
   (k) step for applying static magnetic field, slice selective gradient magnetic field, gradient magnetic field for reading out said signal to said object placed in said measurement space with said defined pulse sequence per each time phase, and for acquiring signal expressing motion of said object and signal of static field non-uniformity distribution of said selected slice,
   (l) step for applying static magnetic field and slice selective gradient magnetic field and gradient magnetic field for reading out said signal with said defined pulse sequence to said object placed in said measurement space per each time phasing, and acquiring signal showing said motion of said object and image information in said selected slice,
   (m) step for removing static magnetic field non-uniformity signal comprising static field non-uniformity by said motion of said object from signal showing image information of said object per each time phase acquired in said step (1), using signal expressing motion of said object acquired in said step (k) and signal showing non-uniformity distribution of said static magnetic field in said selected slice and signal expressing motion of said object acquired by said step (1), and
   (n) step for performing image reconstruction by using signal of which static magnetic field non-uniformity is removed in said step (m).

4. Magnetic resonance imaging method comprising,
(o) step for detecting motion of an object, and for setting plural number of time phase in one period interval of a motion of said object,
(p) step for applying static magnetic field and slice selective gradient magnetic field and gradient magnetic field for reading out said signal to said object placed in the measurement space with said defined pulse, and for acquiring signal expressing motion of said object and signal showing non-uniformity distribution of said static magnetic field in said selected slice,
(q) step for applying static magnetic field and slice selective gradient magnetic field and gradient magnetic field for reading out said signal to the object placed in the measurement space with said defined pulse sequence in every time phase being set, and for acquiring signal expressing said motion of said object and signal showing image information in said selected slice,
(r) step for detecting signal showing irregular motion of said object from said signal expressing motion of said object acquired by said step (p) or step (q) and for removing this detected irregular motion signal from image information acquired in said step (q),
(s) step removing static magnetic field non-uniformity signal from signal having be removed irregular motion signal in said step (r) by using signal expressing motion of said object acquired by said step (p) and step (q) and signal showing static magnetic field non-uniformity distribution in said selected slice and signal expressing said motion of said object per every time phasing being set, and
(t) step for image reconstructing signal acquired in said step (s).

5. A magnetic resonance imaging method according to claims 1 or 4, wherein said signal that shows static magnetic field non-uniformity being acquired in plural number of time phase over one period of a periodical motion of said object is used to correct signal of said same time phasing in said signal expressing imaging information.

6. A magnetic resonance imaging method according to claims 1 or 4, wherein the signal expressing static magnetic field non-uniformity is measured in plural number of time phasing over one period of a motion of said object, and the signal expressing image information is measured continuously to the plural number of images.

7. A magnetic resonance imaging method according to claims 1 or 4, wherein static magnetic field non-uniformity correction is performed after one-dimensional transforming said signal showing static magnetic field non-uniformity and signal expressing image information.

8. A magnetic resonance imaging apparatus comprising,
magnetic field generation means for generating static magnetic field and gradient magnetic field and high frequency magnetic field to measuring space that an object is placed, detecting means for detecting nuclear magnetic resonance signal generated from said object, signal processing means for signal processing nuclear magnetic resonance signal detected by said detecting means,
means for image reconstructing signal processed by this signal processing means,
image display means for displaying the reconstructed image, means for applying static magnetic field and slice selective gradient magnetic field and gradient magnetic field for reading out said signal to said object placed in said measurement space with said defined pulse sequence and for acquiring signal showing non-uniformity of said static magnetic field in said selected slice of said object,
means for applying static magnetic field and slice selective gradient magnetic field and phase encode gradient magnetic field and gradient magnetic field for reading out said signal to said object placed in said measurement space with said defined pulse sequence and for acquiring signal showing image information in said selected slice of said object,
means for removing signal showing said static magnetic field non-uniformity from signal showing said image information and for making signal expressing real image information of said object, and
means for reconstructing image of said object from said signal expressing real image information of said object.

9. A magnetic resonance imaging apparatus comprising,
magnetic field generation means for generating static magnetic field and gradient magnetic field and high frequency magnetic field to measuring space in which an object is placed,
detecting means for detecting nuclear magnetic resonance signal being generated from said object,
signal processing means for signal processing nuclear magnetic resonance signal detected by said detecting means,
image reconstruction means for image reconstructing said signal processed by said signal processing means,
image display means for displaying image reconstructed by said image reconstructing means,
means for applying static magnetic field and slice selective gradient magnetic field and gradient magnetic field for reading out said signal to said object placed in said measurement space with said defined pulse sequence and for acquiring signal showing non-uniformity distribution of said static magnetic field in said selected slice of said object,
means for detecting motion of said object by setting plural number of time phase in one period interval of said motion of said object and acquiring an MR signal showing motion of said object per these each time phasing,
means for applying static magnetic field and slice selective gradient magnetic field and phase encode gradient magnetic field and gradient magnetic field for reading out to said object placed in said measurement space in each time phase in one period interval of said motion of said object with said defined pulse sequence and for acquiring signal showing image information in said selected slice of said object,
means for removing static magnetic field non-uniformity signal including static magnetic field non-uniformity of said motion of said object from signal showing image information of said object in each time phasing by using said signal showing static magnetic field non-uniformity and signal showing motion of said object, and
means for performing image reconstruction using signal that the static field non-uniformity signal is removed.

10. A magnetic resonance imaging apparatus comprising,
magnetic field generation means for respectively generating static magnetic field and gradient magnetic field and high frequency magnetic field to measuring space in which an object is placed, detecting means for detecting nuclear magnetic resonance signal generated from said object, signal processing means for signal processing said nuclear magnetic resonance signal detected by said detecting means, means for image reconstructing said signal processed by said signal processing means, image display means for displaying reconstructed image, means for detecting said motion of said object and setting plural number of time phase in one period interval of said motion of said object, means for applying static magnetic field and slice selective gradient magnetic field and gradient magnetic field for reading out said signal to said object placed in said measurement space with said defined pulse sequence in each time phase that is set and for acquiring signal expressing motion of said object and signal showing non-uniformity distribution of said static magnetic field in said selected slice, means for applying static magnetic field and slice selective gradient magnetic field and gradient magnetic field for reading out said signal to said object placed in said measurement space with said defined pulse sequence per time phase that is set and for acquiring said signal expressing said motion of said object and said signal showing said image information in said selected slice, means for removing static magnetic field non-uniformity signal including static magnetic field non-uniformity by said motion of said object from said signal showing image information of said object in each time phase by using signal expressing motion of said object and signal showing non-uniformity distribution of said static magnetic field in said selected slice and signal expressing motion of said object that is acquired together with said imaging signal, and means for performing image reconstructing by using signal that said static magnetic field non-uniformity signal is removed.

11. A magnetic resonance imaging apparatus comprising, magnetic field generation means for generating static magnetic field and gradient magnetic field and high frequency magnetic field respectively to measuring space in which an object is placed, detecting means for detecting nuclear magnetic resonance signal generated from said object, signal processing means for signal processing said nuclear magnetic resonance signal detected by said detecting means, means for image reconstructing said signal processed by said signal processing means, image display means for displaying reconstructed image, means for detecting motion of said object and setting plural number of time phase in one period interval of said motion of said object, means for applying static magnetic field and slice selective gradient magnetic field and gradient magnetic field for reading out said signal with said defined pulse sequence in each time phase that is set and acquiring signal expressing motion of said object and non-uniformity distribution of said static magnetic field in said selected slice, means for applying static magnetic field and slice selective gradient magnetic field and gradient magnetic field for reading out said signal with said defined pulse sequence in each time phase set and acquiring signal expressing motion of said object and signal showing image information in said selected slice, means for detecting signal showing an irregular motion of said motion from signal expressing said motion of said object and removing said detected irregular motion signal from information, means for removing static magnetic field non-uniformity signal from image signal that said irregular motion signal is removed by using signal expressing motion of said object and signal showing non-uniformity distribution of said static magnetic field in said selected slice and signal expressing motion of said object in each time phase that is set, and means for image reconstructing from signal that the static field non-uniformity signal is removed.

12. The magnetic resonance imaging method according to claim 2, wherein correction for motion in step (h) does not adversely affect the correction for the static magnetic field non-uniformity.

13. The magnetic resonance imaging method according to claim 1 or claim 4, wherein said signal showing non-uniformity distribution of said static magnetic field is acquired by continuously alternating the polarity of the read out gradient magnetic field without applying the phase encode gradient magnetic field, and said signal showing real image information is acquired by continuously alternating the polarity of the read out gradient magnetic field, with the phase encode gradient magnetic field being applied discretely.

* * * * *